United States Patent [19]
Murthy et al.

[11] Patent Number: 5,633,386
[45] Date of Patent: May 27, 1997

[54] COMMERCIAL PROCESS FOR THE MANUFACTURE OF FLUCONAZOLE AND INTERMEDIATES USEFUL IN THE MANUFACTURE THEREOF

[75] Inventors: Keshava Murthy; Gamini Weeratunga, both of Brantford; Derek J. Norris, Oakville; Stephen Horne, Burlington; Derrick L. J. Clive, Edmonton, all of Canada

[73] Assignee: ACIC (Canada) Inc., Brantford, Canada

[21] Appl. No.: 470,636

[22] Filed: Jun. 6, 1995

[30] Foreign Application Priority Data

Dec. 23, 1994 [CA] Canada ................................. 2139079

[51] Int. Cl.$^6$ ........................................... C07D 403/10
[52] U.S. Cl. ......................................... 548/266.6
[58] Field of Search ........................................ 548/266.6

[56] References Cited

U.S. PATENT DOCUMENTS 5,484,936 1/1996 Veinberg et al. ..................... 548/265.6

Primary Examiner—Patricia L. Morris
Attorney, Agent, or Firm—Ivor M. Hughes; Neil H. Hughes; Marcelo K. Sarkis

[57] ABSTRACT

A process for making Fluconazole is provided comprising carrying out the following scheme of reaction:

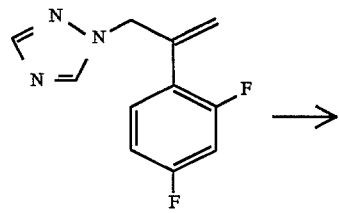

5

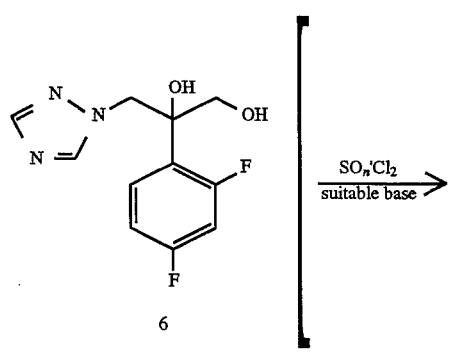

6

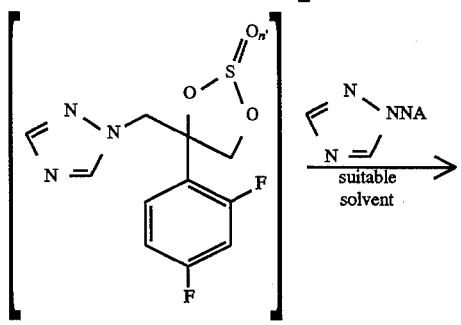

7 where n' = 1
8 where n' = 2

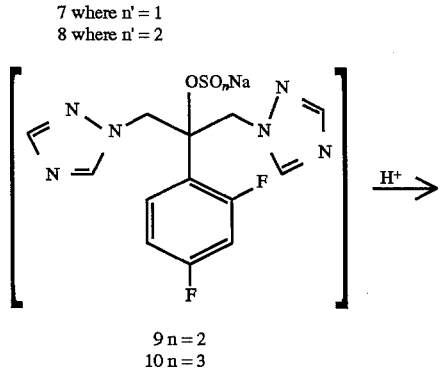

9 n = 2
10 n = 3

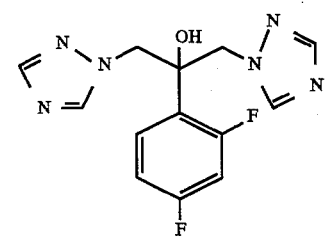

Fluconazole

7 Claims, No Drawings

COMMERCIAL PROCESS FOR THE MANUFACTURE OF FLUCONAZOLE AND INTERMEDIATES USEFUL IN THE MANUFACTURE THEREOF

APPLICATION

This invention relates to novel processes for the manufacture of Fluconazole, novel intermediates useful in the manufacture of Fluconazole, and novel processes for the manufacture of the intermediates.

Fluconazole, α-(2,4-Difluorophenyl)-α-(1H-1,2,4,-triazol-1-ylmethyl)-1H-1,2,4-triazole-1-ethanol; 2,4-Difluoro-α-α-bis(1H-1,2,4-triazol-1-ylmethyl)benzyl alcohol; 2-(2,4-difluorophenyl)-1,3-bis(1H-1,2,4-triazol-1-yl)-propan-2-ol, is an antifungal agent and presents the following structure:

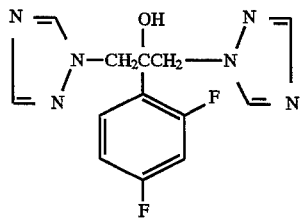

I

Canadian Letters Patent No. 1,170,263 [corresponding to U.S. Pat. No. 4,416,682 and European Patent Application Ser. No. 0044605 (published Jan. 27, 1982)] purports to teach compounds having the following structure:

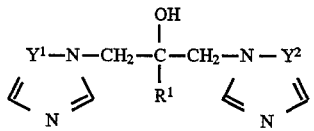

wherein $Y^1$ and $Y^2$ may be =N—, and $R^1$ may be aryl (page 1, line 16) wherein aryl may be substituted by "halogen (e.g., fluorine, chlorine or bromine)" (page 2, lines 17–18) and processes for the manufacture thereof (see for example page 7, line 1 to page 9, line 21).

One of the molecules:

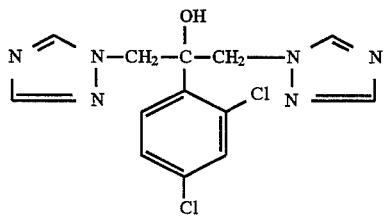

1,3-Bis-(1,2,4-triazol-1-yl)-2-2,4-dichloro-phenyl)-propan-2-ol is alleged to be teratongenic (alleged at page 3, line 17 of Canadian Letters Patent No. 1,181,076):

... foetuses from animals treated with the compound in which R=2,4-dichlorophenyl at 20 mg/kg body weight showed malformations, in particular cleft palates. Examination of visceral and skeletal features revealed that this compound was teratogenic at doses as low as 1 mg/kg, e.g., presence of microphthalmia, increased incidence of dilation of the ureters and renal pelves, delay in ossification of some bones, and increased incidence of a $14^{th}$ pair of ribs.

Also, the compound in which R=4chlorophenyl was extremely embryotoxic at 20 mg/kg, whilst the compound in which R=2-chlorophenyl produced external abnormalities (cleft palate) at this dose. These compounds are specifically disclosed as "Compounds 1 and 9," respectively, in Table 1 of the ICI applications. In addition, the compounds in which R=3, chlorophenyl and R=4-Bromophenyl, which are claimed but not specifically disclosed in the ICI applications, also produced the same external abnormalities at 20 mg/kg. The latter compounds was also embryotoxic at this dose (page 4, line 16-page 5, line 9).

It is clear that, if true, this useless compound is claimed to be one of the compounds of the purported invention of Canadian Letters Patent No. 1,170,263.

The said Canadian Letters Patent No. 1,170,263 and corresponding U.S. patent and European application referred to above disclose processes for the manufacture of Fluconazole, wherein $R^1$ is aryl substituted by the halogen (fluorine) and $Y^1$ and $Y^2$ is =N—.

Canadian Letters Patent No. 1,181,076 discloses only Fluconazole and was actually filed in Canada on Jun. 4, 1982. European Patent Application Ser. No. 0044605 (corresponding to Canadian letters Patent No. 1,170,263) was published Jan. 27, 1982. Canadian Letters Patent No. 1,181,076 discloses the same processes as Canadian Letters Patent No. 1,170,263 and European Patent Application Ser. No. 0044605.

Canadian Letters Patent No. 1,182,822 relates to an intermediate for making Fluconazole.

Several methods for the synthesis of Fluconazole are reported in the literature (EP 0096569; ES 9002961; CA 1,191,076; CA 1,182.822; CA 1,170,263; ES 9502961; GB 2099818; U.S. Pat. No. 4,404,216; ES 549020; ES 549684; ES 549022; ES 549021; EP 83-303244) and some prominent ones are listed below:

(a) The reaction of 1,2,4-Triazole with compound of formula II-B gives Fluconazole. Compound II was prepared according to the following scheme (Canadian Letters Patent No. 1,181,076):

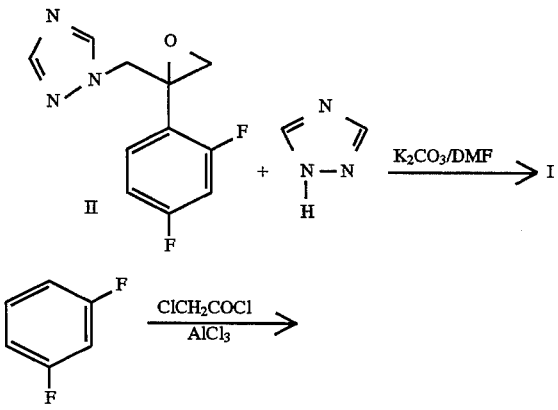

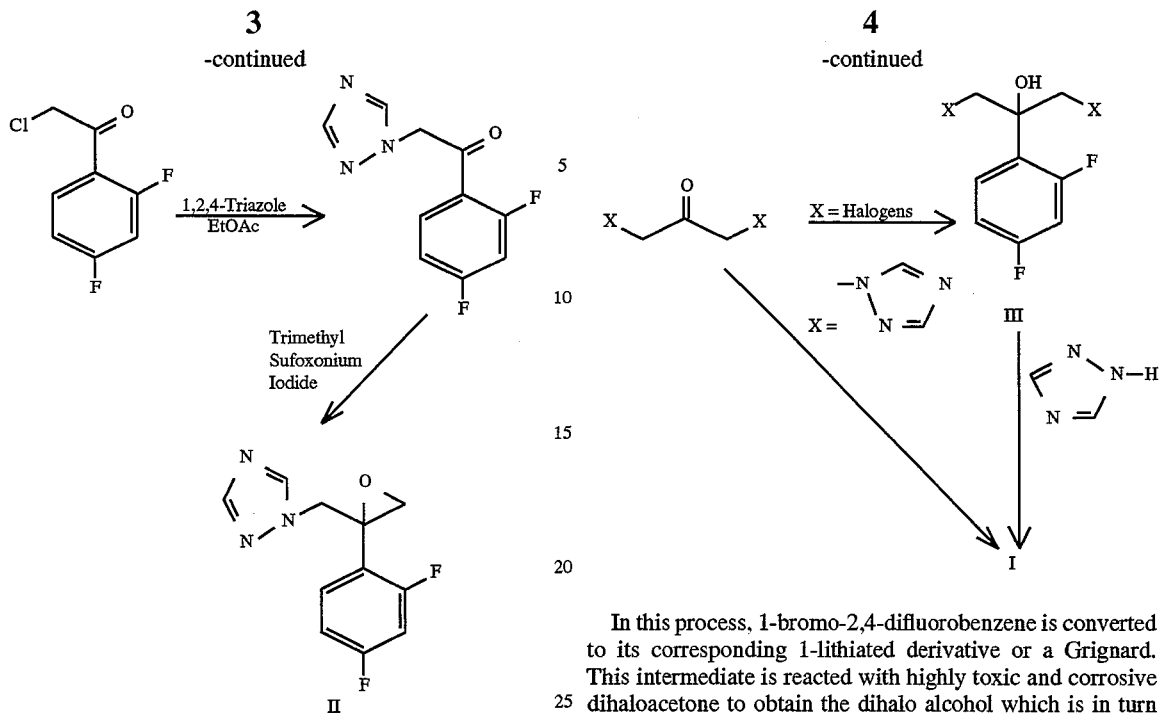

This method involves conversion of epoxide (II) to Fluconazole (44% yield). Epoxide (II) was prepared from commercially-available 1,3-difluorobenzene over three steps. Although the chemistry involved is not too difficult, the yields obtained in Steps 2–4 are very low. The overall yield in this process is difluorobenzene→fluconazole is about 4%.

(b) Fluconazole is also obtained by reacting 1,2,4-triazole with a compound of formula III, which in turn is prepared according to the following scheme.

Alternatively, Compound I can be obtained by the reaction of 1,3-ditriazole acetone with the corresponding Grignard of difluorobenzene (CA 1,182,822; CA 1,181,076; ES 549020).

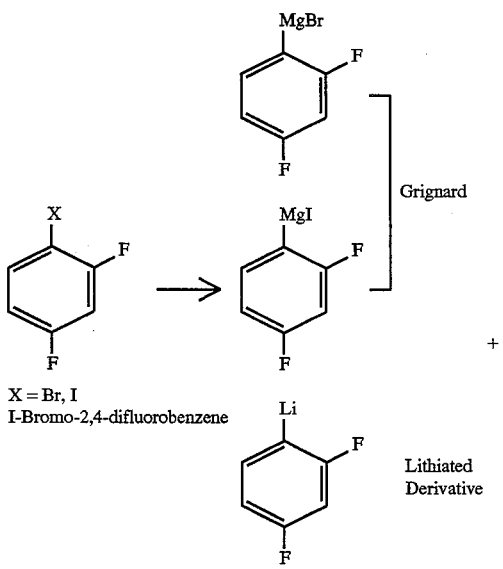

In this process, 1-bromo-2,4-difluorobenzene is converted to its corresponding 1-lithiated derivative or a Grignard. This intermediate is reacted with highly toxic and corrosive dihaloacetone to obtain the dihalo alcohol which is in turn converted to Fluconazole.

Lithiation of 1-bromo-2,4-difluorobenzene involves the use of the highly sensitive (to moisture, air), highly flammable, and corrosive compound n-butyl lithium. Also, the solvents used in both lithiation and Grignard reactions are diethyl ether or tetrahydrofuran. These solvents are extremely flammable and hazardous. The above-mentioned reagents and solvents are dangerous to handle in large quantities, and hence this method is not very attractive for large-scale commercial production.

Compared to these two methods, Applicant's synthesis involves reaction conditions and reagent (raw materials) that are suitable for synthesis on a large scale.

Applicant has previously filed Canadian Patent Application Ser. No. 2,106,032 on Sep. 13, 1993, entitled Methods for the Manufacture of Fluconazole and Forms Thereof, Intermediates Useful in the Manufacture Thereof, and Combinations Comprising Fluconazole. In that Application, intermediate XIII, 3-(1H-1,2,4-triazol-1-41)-2-(2,4-difluorophenyl)-1-propene, set out below was made and used to produce Fluconazole.

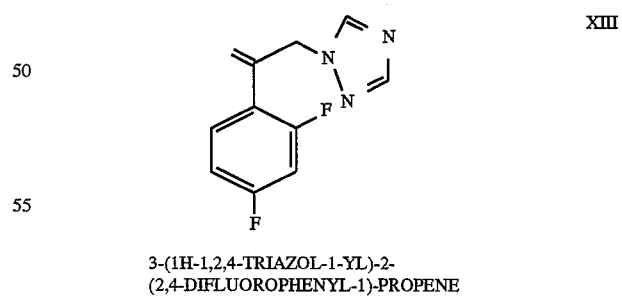

3-(1H-1,2,4-TRIAZOL-1-YL)-2-
(2,4-DIFLUOROPHENYL-1)-PROPENE 3-(1H-1,2,4-triazol-1-YL)-2-(2,4-difluorophenyl)-1-propene, XIII.

Descriptions of Processes to make XIII are described in the application schematically at pages 8, 10 and 12 as follows:

1. 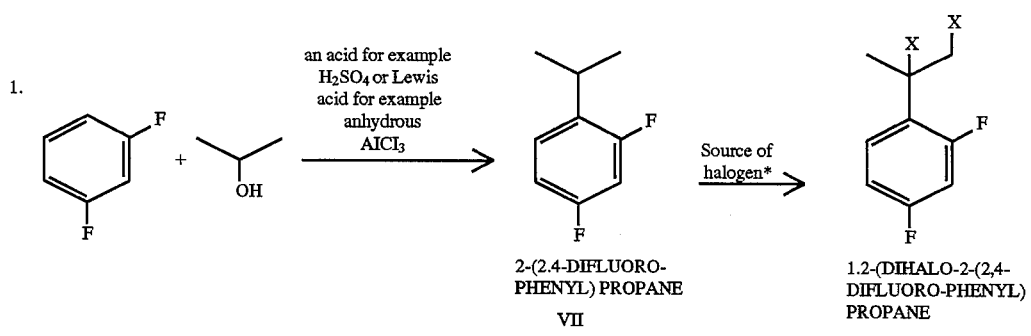
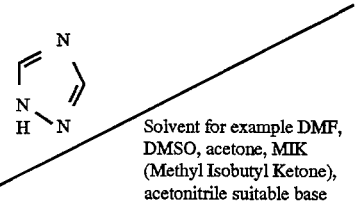
3(1H-1,2,4-TRIAZOL-1-YL)-2-
(2,4-DIFLUOROPHENYL)-1-PROPENE
XIII
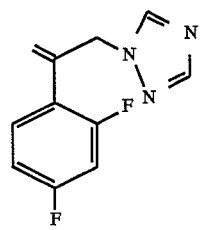
2. 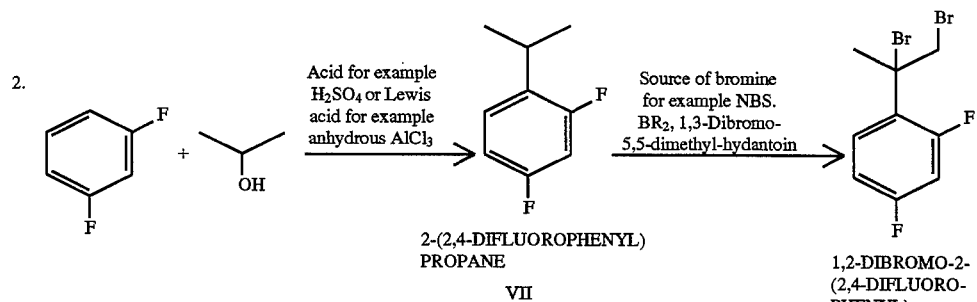
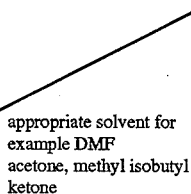
3(1H-1,2,4-TRIAZOL-1-YL)-2-
(2,4-DIFLUOROPHENYL)-1-PROPENE
XIII
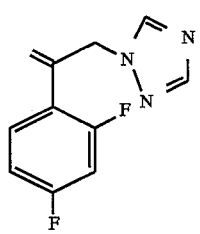

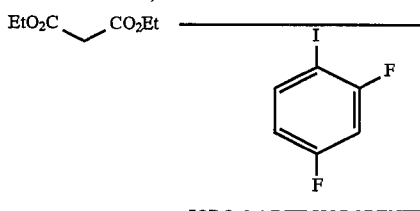
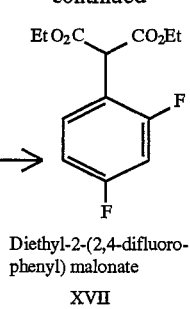
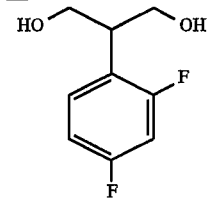
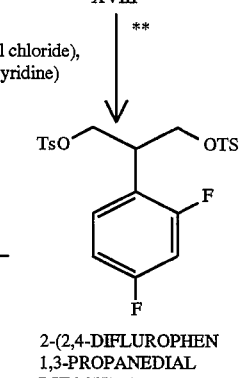

**Instead of tosylate, one can use any leaving group e.g. Br, I, Cl

Detailed processes setting out procedures for making intermediate XIII are set out in Examples 5 and 8 at pages 28–29 as follows:

EXAMPLE 5

3-(1H-1,2,4-TRIAZOL-1-YL)-2-(2,4-DIFLUOROPHENYL)-1-PROPENE XIII

To a solution of ditosylate (XIX) 350 mg, 0.7 mmol in 6 mL acetone, $K_2CO_3$ (390 mg, 2.8 mmol) and triazole (110 mg, 1.5 mmol) were added. The reaction was refluxed for 18 h and then cooled to room temperature and filtered. The solvent was removed, the crude material subjected to column chromatography on silica gel, and eluted with EtOAc to give 125 mg (81%) of the title compound.

$^1$H NMR (CDCl$_3$, 250 MHz), δ5.18 (2H, s), 5.35 (1H, s), 5.46 (1H, s), 6.7–6.88 (2H, m), 7.12–7.25 (1H, m), 7.89 (1H, s), 8.70 (1H, s).

EXAMPLE 8

3-(1H-1,2,4-TRIAZOL-1-YL)-2-(2,4-DIFLUOROPHENYL)-1-PROPENE XIII 5 g (15.9 mmol) of 1,2-dibromo-2-(2,4-difluorophenyl)propane VIII and 3.3 g (48 mmol) of 1,2,4-triazole in DMF was refluxed for 15 hours. The reaction mixture was cooled down to room temperature, water (40 mL) was added and product was extracted with EtOAc (2×50 mL). The EtOAc phase was washed with water and dried (Na$_2$SO$_4$). Evaporation of the solvent under reduced pressure and purification of the residue on a silica gel column with ethyl acetate as the eluent, furnished the title compound (1.05 g, 30%).

$^1$H NMR (CDCl$_3$, 250 MHz), δ5.18 (2H, s), 5.35 (1H, s), 5.46 (1H, s), 6.7–6.88 (2H, M), 7.12–7.25 (1H, m), 7.89 (1H, s), 8.70 (1H, s).

The manufacture of a further intermediate XIX is described at page 30 as follows:

EXAMPLE 12

2-(2,4-DIFLUOROPHENYL)-1,3-PROPANEDIOL DI-TOSYLATE XIX

To a solution of the diol XVIII (1.1 g, 5.8 mmol), 2.8 mL (34.8 mmol) pyridine and catalytic DMAP in 30 mL CH$_2$Cl$_2$, TsCl (4.5 g. 23.4 mmol) was added portion wise at 5° C. The reaction was stirred at room temperature for 16 hours, then washed with 1M HCl, water, brine and dried over MgSO$_4$. The solvent was removed in vacuo, the crude material passed through a silica gel column, and eluted with EtOAc/Hexane 1:3 to give 2 g (70%) of the title compound.

$^1$H NMR (CDCl$_3$, 60 MHz) δ2.4 (3H,s), 3.52 (1H, d, J=9.5 Hz), 4.19 (4H, d, J=9.5 Hz), 6.5–7.2 (3H, m), 6.5–7.2 (3H, m), 7.2–7.7 (8H, AA'BB').

We have now developed using intermediate XIII as a starting point (as starting material), new processes for making Fluconazole and novel intermediates therefore. The new processes are highly efficient and at least one of the processes (what we term the "sulphate process") is suitable for synthesis of Fluconacole on a commercial scale.

It is therefore an object of this invention to provide new processes for the manufacture of Fluconazole and new processes for the manufacture of intermediates useful in the manufacture of Fluconazole from starting materials which are readily available commercially, easily handled, relatively inexpensive, and relatively safe to use.

Further and other objects of the invention will be realized by those skilled in the art from the following summary of the invention and detailed description of embodiments thereof.

According to one aspect of the invention, processes for making Fluconazole are provided and illustrated schematically as follows:

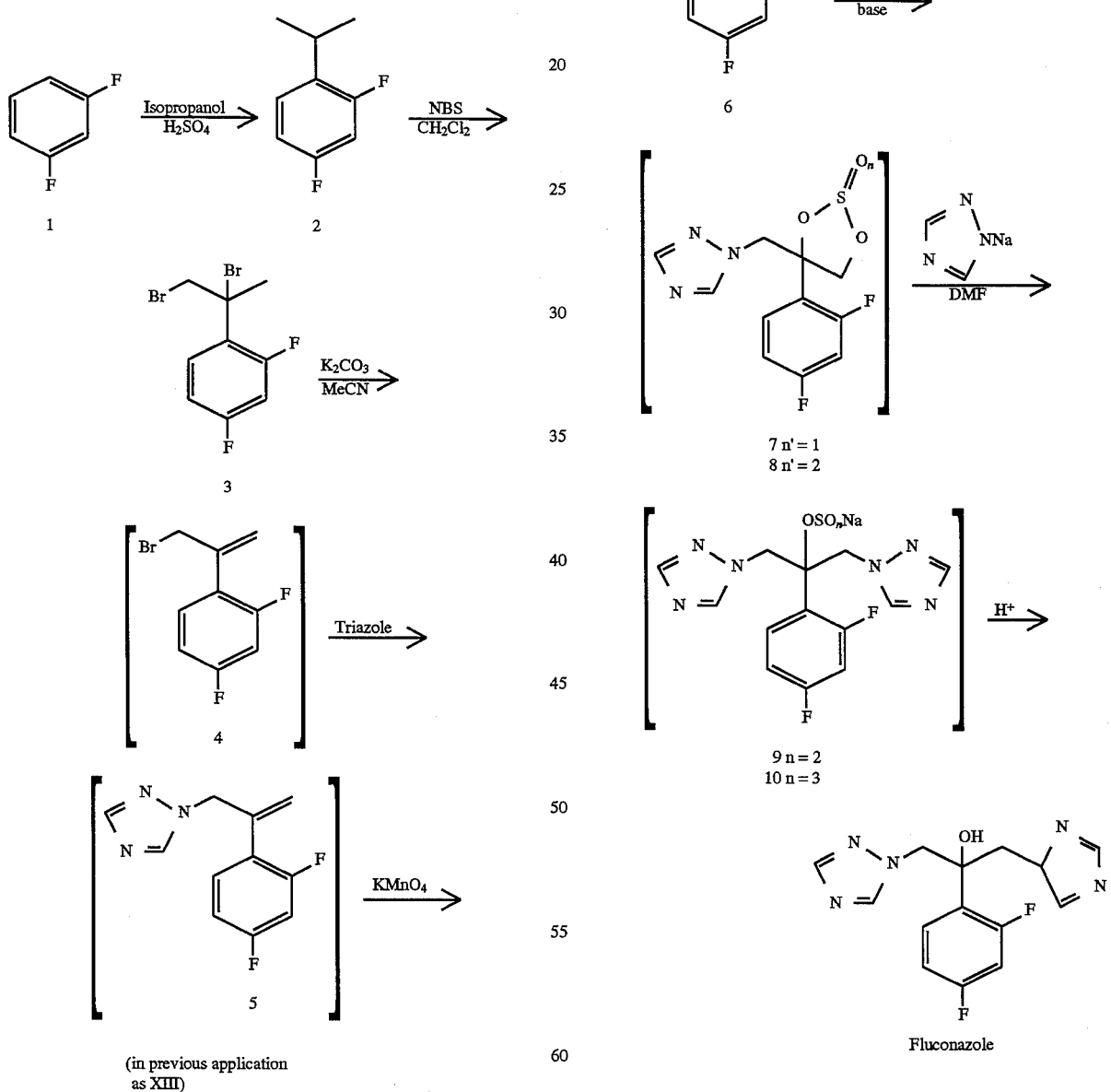
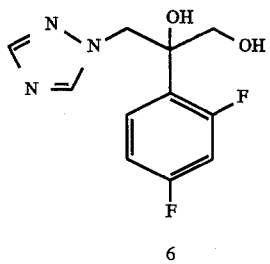

In one embodiment, Fluconazole may be made according to what we term the "sulphate process" set out below:

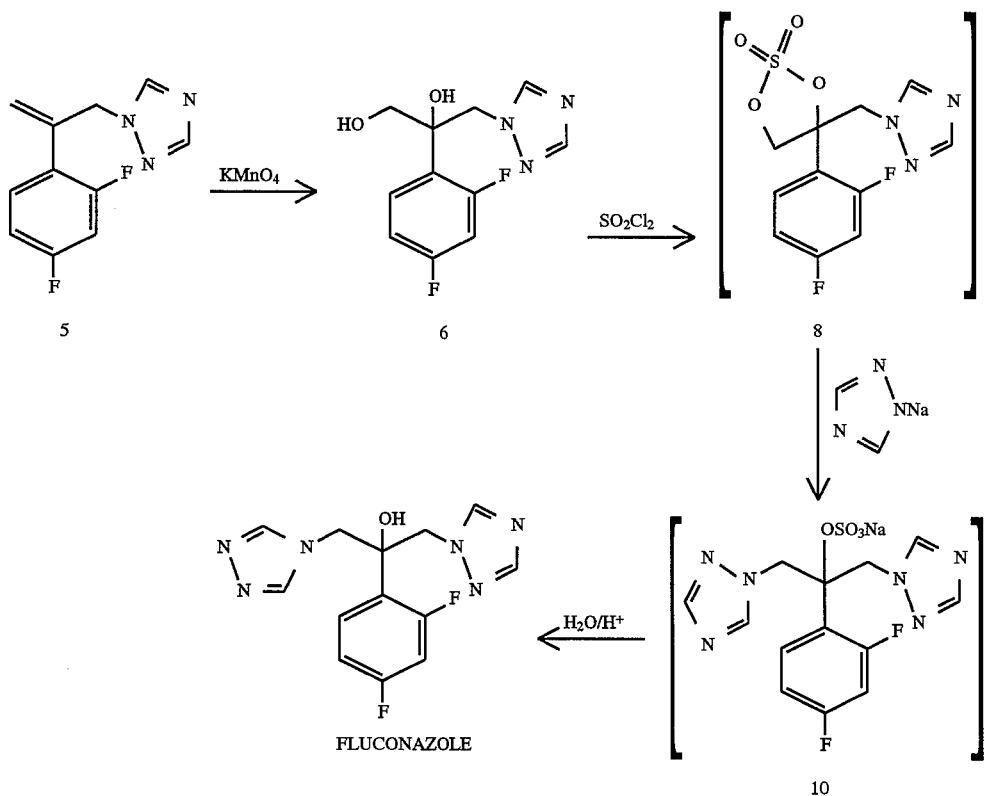

FLUCONAZOLE

Initially, we prepared the cyclic sulphite 7 directly from diol 6 in high yield by reaction of 6 with thionyl chloride (SOCl$_2$) in the presence of a base at low temperature. Use of 7 in reactions with 1,2,4-triazole and various derivatives, generated only low yields of fluconazole. Despite many attempts to improve the efficiency of this reaction, yields of isolated fluconazole remained low due to competitive elimination processes and competitive nucleophilic attack at the sulphur atom.

To overcome these problems, we attempted the use of the corresponding cyclic sulphate (as sulphates are more reactive than sulphites in displacement reactions). We therefore expected to minimize elimination reactions. Further, the preponderance for nucleophilic attack at the sulphate sulphur atom was expected to be minimized relative to that in the sulphite intermediate, as the former would necessarily involve a pentavalent intermediate in the transition state. In preliminary experiments, many attempts were made to oxidize the cyclic sulphite 7 to the desired sulphate. For example, attempts to oxidize 7 with KMnO$_4$/BnEt$_3$NCl, RuO$_2$/NaOCl, RuCl$_3$/NaIO$_4$, m-CPBA, and dimethyl dioxirane were uniformly unsuccessful. These methods frequently resulted in overoxidation and ring cleavage processes.

However, utilizing suitable solvents (deuterated solvents were used in the initial experimental studies), the sulphate 8 was generated from 6 using SO$_2$Cl$_2$ (sulphuryl chloride) and K$_2$CO$_3$ as reagents. Sulphate 8 was observed by $^1$H NMR spectroscopy. Although 8 could be isolated by workup of the reaction mixture and characterized by spectrospic methods, it proved to be too unstable for prolonged storage. Thus, the generation of 8 in situ followed by reaction with the sodium salt of 1,2,4-triazole directly afforded fluconazole (through the thermal expulsion of SO$_3$ in situ). The protonated form of the sodium sulphonate intermediate 10, which originates from 8, has been isolated in a pure state and is readily characterized. Using an acidic hydrolysis, 10 was transformed into fluconazole, thereby confirming the intermediacy of the cyclic sulphate and the sodium sulphonate intermediates as novel entities in this pathway to fluconazole.

Thus the present process involves intermediates distinctly different from those utilized previously. Mechanistically, in a preferred embodiment, the process involves attack by a metallic salt of 1,2,4-triazole on a cyclic sulphate (for example 8) which leads to metallic sulphonate (for example sodium sulphonate) and alkoxide derivatives which then both require a proton source to be converted to fluconazole O-sulphonic acid and fluconazole, respectively. The use of metallic salts of 1,2,4-triazole is preferable in this process as these reagents enhance the reaction rate compared to 1,2,4-triazole itself, in other words, such reagents display a higher proclivity to participate in displacement reactions. The significantly higher yield of fluconazole (49–55% from the diol 6) in the current process illustrates the advantage of the cyclic sulphate versus any prior process including the use of an epoxide in Canadian Letters Patent 1,181,076. In this Canadian Patent, the single step transformation of an epoxide to fluconazole proceeded in a reported yield of 44% (42% according to our recalculation).

Thus we have made novel processes for making fluconazole and novel intermediates useful for making Fluconazole. Further intermediates 6; 7 when n=1; 8 when n=2, 9 when n=2 and 10 when n=3 are novel. (It should be noted that no one skilled in the art would attempt to achieve the manufacture of Fluconazole directly from intermediate 6. The addition of triazole or sodium triazole to 6 would not produce Fluconazole.)

The invention will now be illustrated with reference to the following examples:

EXAMPLE 1

2-(2,4-Difluorophenyl)-2,3-dihydroxypropyl-1H-1,2,4-triazole (6)

2-Bromo-2-(2,4-difluorophenyl)-1-bromopropane (3) (20.0 g, 63.7 mmol) was dissolved in acetonitrile (300 mL) at 20° C. and $K_2CO_3$ (17.6g, 127 mmol) was added in one portion with efficient stirring. The reaction mixture was heated to reflux for 11 hours and then cooled to 20° C. 1,2,4-Triazole (8.80 g, 127 mmol) was added with stirring and the mixture was heated to reflux for 2 hours. The reaction mixture was cooled to 20° C. and filtered, and 175 mL of acetonitrile was removed by evaporation. The solution was cooled (5° C.) and treated dropwise with a solution of $KMnO_4$ (10.07 g, 63.7 mmol) in water (300 mL) over 45 minutes. After the addition, the black precipitate was removed by filtration through Celite at 20° C. and the filtrate was treated with $NaHSO_3$ (7.2 g) with stirring. The aqueous layer was separated, saturated with NaCl, and extracted with EtOAc (3×400 mL). The combined organic layers were washed with saturated $NaHCO_3$ solution (2×300 mL), and dried over $Na_2SO_4$. The aqueous solution was evaporated to half volume and extracted with EtOAc (2×600 mL). Evaporation of the combined EtOAc layers left a crude product which was chromatographed on silica gel (EtOAc/hexanes/EtOH 15:5:1) afforded 27% of 6 as a white crystalline powder.

$^1$H NMR (250 MHz, $CDCl_3+D_2O$) δ3.75 (d, 1H), 4.0 (d, 1H), 4.75 (q, 2H), 6.7–6.9 (m, 2H), 7.5–7.6 (m, 1H) 7.90 (s, 1H), 7.98 (s, 1H).

EXAMPLE 2

(The "Sulphate Process") Fluconazole

A 3-necked flask, fitted with a mechanical stirrer, condenser, and addition funnel was charged with 6(4.00 g, 15.7 mmol) and ethanol-free chloroform (60 mL) under a nitrogen atmosphere. Stirring was initiated and powdered $K_2CO_3$ (5.3 g, 32 mmol) was introduced in one portion. $SO_2Cl_2$ (1.3 mL, 16 mmol) was added dropwise at 20° C. at a rate such that the internal temperature remained below 30° C. After the completion of the addition, the mixture was stirred at 20° C. for 15 minutes and then was heated to reflux for 2 hours. The chloroform was then removed by distillation and to the solid residue was added dry DMF (35 mL) at 0° C. followed by the sulphate 8. Solid 1,2,4-triazole, sodium derivative (4.8 g, 90%, 48 mmol) was added in portions maintaining the temperature below 5° C. The reaction suspension was allowed to reach room temperature and was then warmed to 65° C. for 5 hours during which time the evolution of an acidic gas was observed through the condenser. The reaction was cooled to 20° C. and treated with water (10 mL) and the DMF was distilled under reduced pressure. The aqueous residue was extracted with EtOAc (3×20 mL) and the combined extracts were dried ($Na_2SO_4$) and evaporated. Crystallization of the residue afforded 1.35 g (29%) of fluconazole. The aqueous phase was evaporated to dryness and the residue was stirred with 20% $H_2SO_4$ (35 mL) and EtOAc (35 mL) for 20 hours at 20° C. for 19 hours. The mixture was then basified with 50% NaOH to pH 11 and the separated aqueous phase was extracted with EtOAc (3×20 mL). The combined extracts were dried ($Na_2SO_4$) and evaporated. The residue was chromatographed with the mother liquor from the crystallization (silica, 5% MeOH/$CH_2Cl_2$) to obtain 1.0 g (20%) of fluconazole (the complete isolated yield of fluconazole is 49% in this experiment and has been as high as 54% previously). The resultant compound was compared with an authentic sample of Fluconazole and they were found to be identical.

Thus we have described new processes for making Fluconazole. The processes are more efficient than those previously described. They are commercially viable.

As many changes can be made to the examples without departing from the scope of the invention, it is intended that all material contained in the examples shall be interpreted as illustrative of the invention and not in a limiting sense.

The embodiments of the invention in which an exclusive property or privilege is claimed are as follows:

1. A process for making Fluconazole comprising the following scheme:

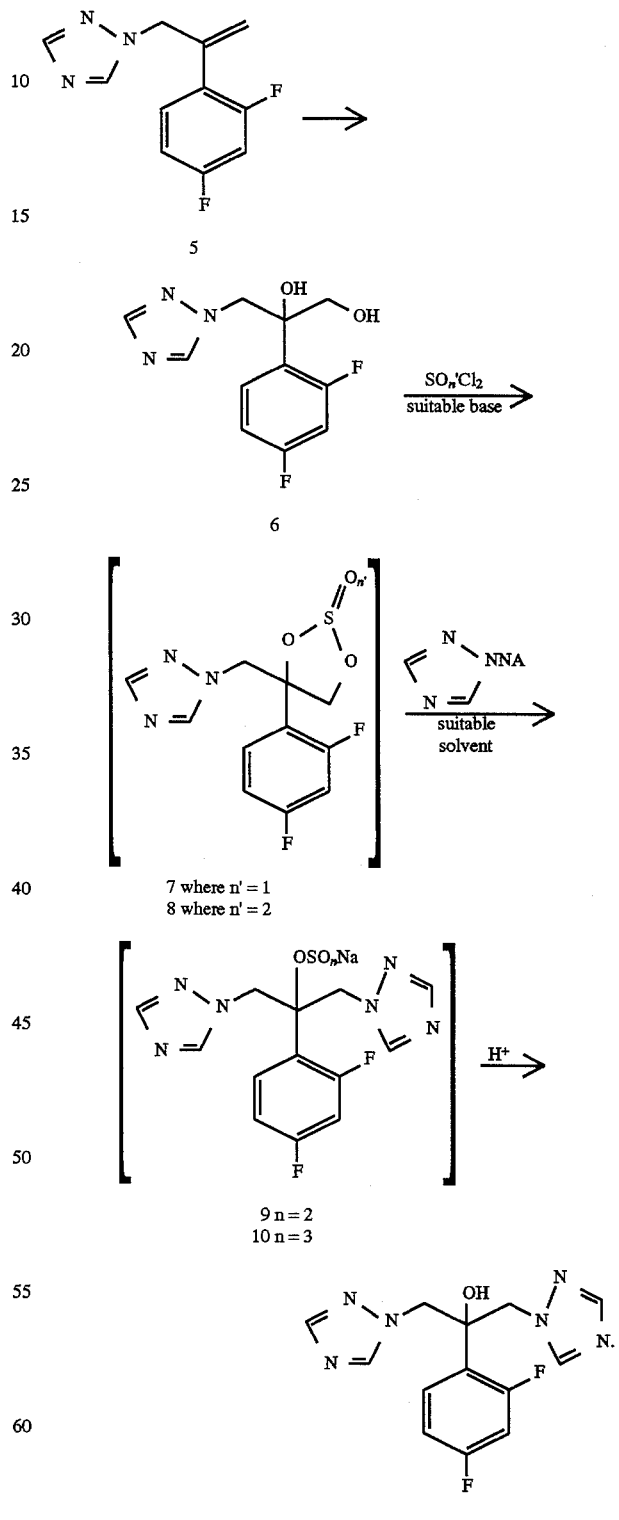

2. The process making Fluconazole comprising the following scheme:

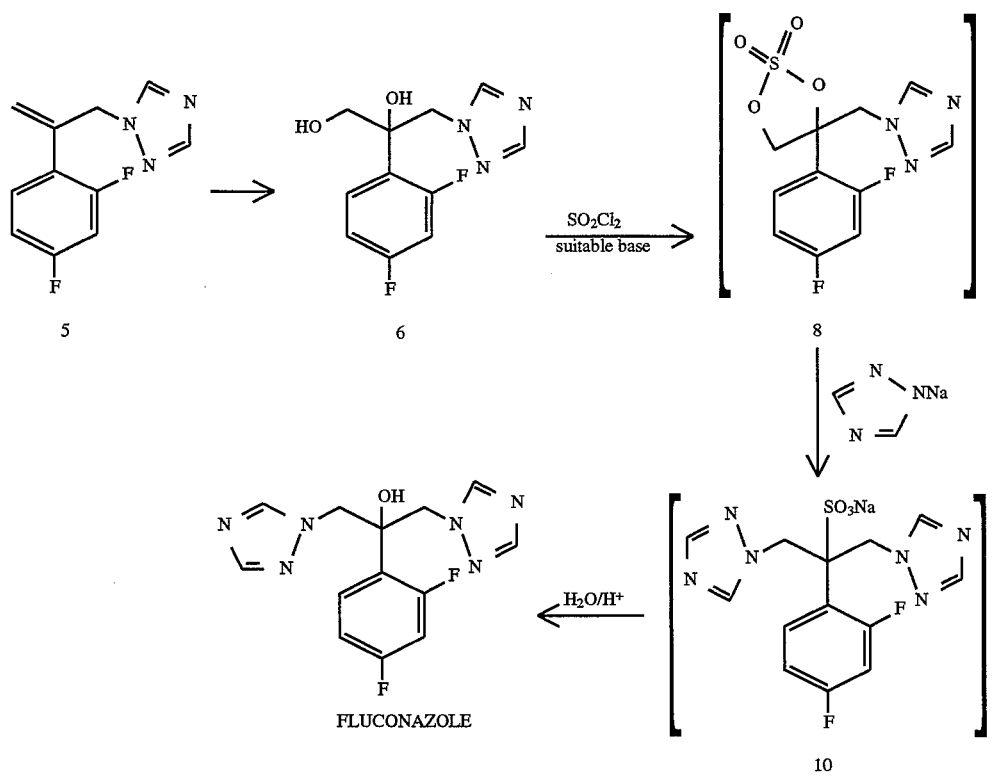

3. The process of claim 1 or 2 wherein the step of making the diol (6) from intermediate (5) is carried out in the presence of potassium permanganate ($KMnO_4$).

4. A process for making Fluconazole by hydrolyzing:

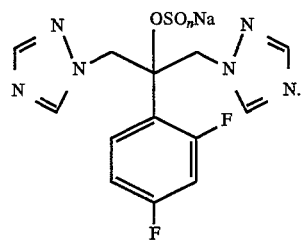

9 n = 2
10 n = 3

5. The process of making Fluconazole by hydrolyzing:

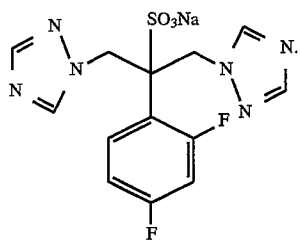

6. The process of claim 5 wherein:

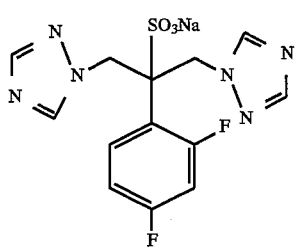

is manufactured by reacting:

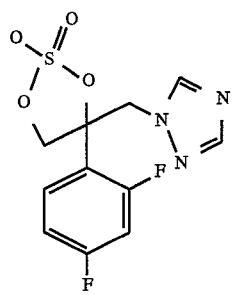

with sodium triazole.

7. The process of claim 5 or 6 further comprising the resultant product to produce Fluconazole.

* * * * *